United States Patent
Li et al.

(10) Patent No.: US 8,706,423 B2
(45) Date of Patent: Apr. 22, 2014

(54) CHEMICAL REACTION-TYPE METAHEURISTIC

(75) Inventors: Victor On-Kwok Li, Midlevels (HK); Albert Yun Sang Lam, Yuen Long (HK)

(73) Assignee: Jang Partners, LLC, Wilmington, DE (US)

( * ) Notice: Subject to any disclaimer, the term of this patent is extended or adjusted under 35 U.S.C. 154(b) by 849 days.

(21) Appl. No.: 12/498,085

(22) Filed: Jul. 6, 2009

(65) Prior Publication Data

US 2010/0057650 A1    Mar. 4, 2010

Related U.S. Application Data

(60) Provisional application No. 61/093,099, filed on Aug. 29, 2008.

(51) Int. Cl.
  *G01N 33/48* (2006.01)
  *G06F 19/12* (2011.01)
  *G06F 19/10* (2011.01)

(52) U.S. Cl.
  CPC ............... *G06F 19/12* (2013.01); *G06F 19/10* (2013.01)
  USPC .......................................................... 702/19

(58) Field of Classification Search
  CPC ................................. G06F 19/10; G06F 19/12
  USPC .......................................................... 702/19
  See application file for complete search history.

(56) References Cited

U.S. PATENT DOCUMENTS

| | | | |
|---|---|---|---|
| 5,778,317 A | 7/1998 | Kaminsky | |
| 5,796,625 A | 8/1998 | Scepanovic et al. | |
| 5,897,628 A | 4/1999 | Kitano | |
| 6,055,523 A | 4/2000 | Hillis | |

OTHER PUBLICATIONS

Boisson et al arXiv:0811.0514v1 [q-bio.QM] Nov. 4, 2008.*
Krasnodor et al. IEEE Transactions on Evolutionary Computation, 9, No. 5, 474-488, 2005.*
Flores et al. The 2003 Congress on Evolutionary Computation, 2003. CEC '03. vol. 4, pp. 2338-2345.*
Coleman et al. Journal of Global Optimization, 4, 171-185,1994.*
Duman, E. et al., "The quadratic assignment problem in the context of the printed circuit board assembly process," Computers & Operations Research 34 (2007) 163-179. Online Jun. 29, 2005 sciencedirect.com.
Miranda, G. et al., "A performance guarantee heuristic for electronic components placement problems including thermal effects," Computer & Operations Research (2005) 2937-2957. Online Jul. 19, 2004 sciencedirect.com.

* cited by examiner

*Primary Examiner* — Michael Borin

(57) ABSTRACT

Subject matter disclosed herein relates to various embodiments of a chemical reaction-type metaheuristic. According to an embodiment, solutions to an objective function can be determined by iteratively searching for a minimum energy state of one or more interactions of molecules in a chemical reaction. The molecules in the chemical reaction can be assigned to represent the possible outcomes of the objective function. In a specific embodiment, the interactions of the molecules can modeled as on-wall ineffective collisions, decompositions, inter-molecular ineffective collisions, and synthesis. The type of interaction can affect where the next molecular structure is searched.

18 Claims, 9 Drawing Sheets

CHEMICAL REACTION-TYPE METAHEURISTIC

CROSS-REFERENCE TO RELATED APPLICATION

The subject application claims the benefit of U.S. Provisional Application Ser. No. 61/093,099, filed Aug. 29, 2008, which is incorporated herein by reference in its entirety.

FIELD

The subject matter of this patent application relates to computational problem-solving and, more particularly, to the use of heuristics or metaheuristics.

BACKGROUND

As is well-known, a variety of computational problems are difficult to solve using conventional computational techniques. For example, applying such techniques may require large amounts of time, computing power, energy, resources or the like, to achieve a solution. However, while it may remain difficult to achieve or obtain a solution, nonetheless, it may be possible to apply computational approaches that provide acceptable results without expending such large amounts of time, computing power, energy, resources or the like. It remains desirable to develop such approaches for particular types of problems.

BRIEF DESCRIPTION OF THE DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description when read with the accompanying drawings in which:

Figure 1:
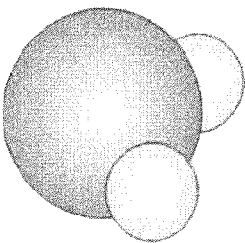
FIG. 1 illustrates an example computational profile of a molecule.
Figure 2A:
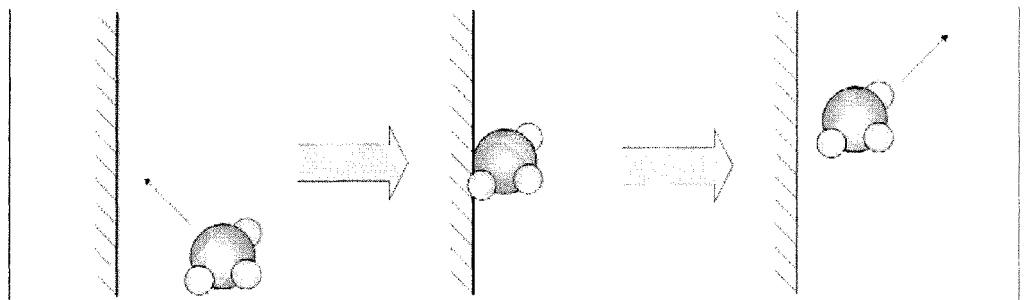
FIG. 2 illustrates four example elementary reactions that may be modeled in accordance with one or more embodiments for a chemical reaction-type metaheuristic.
Figure 2B:
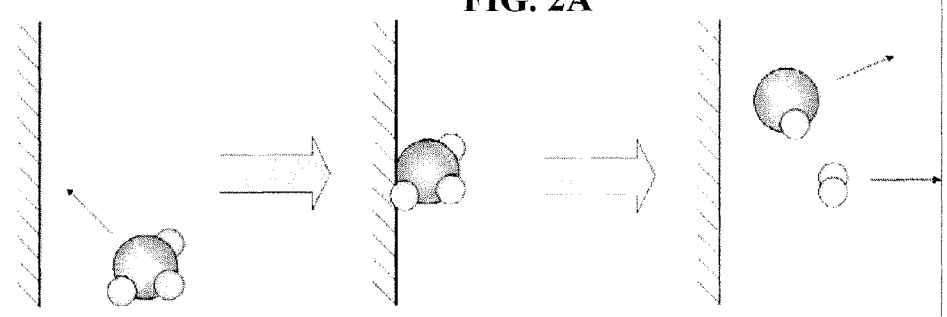
Figure 2C:
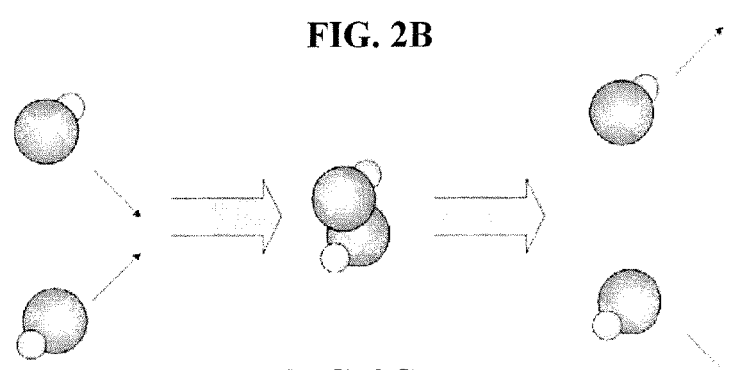
Figure 2D:
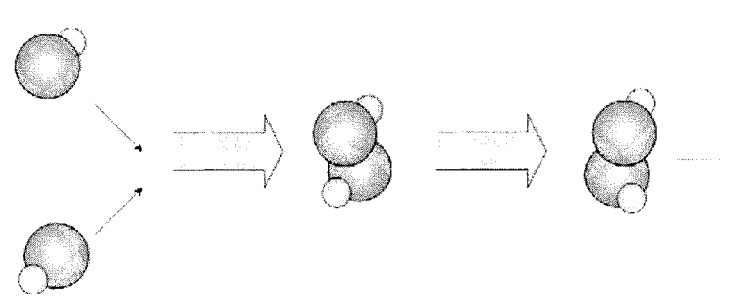
Figure 3A:
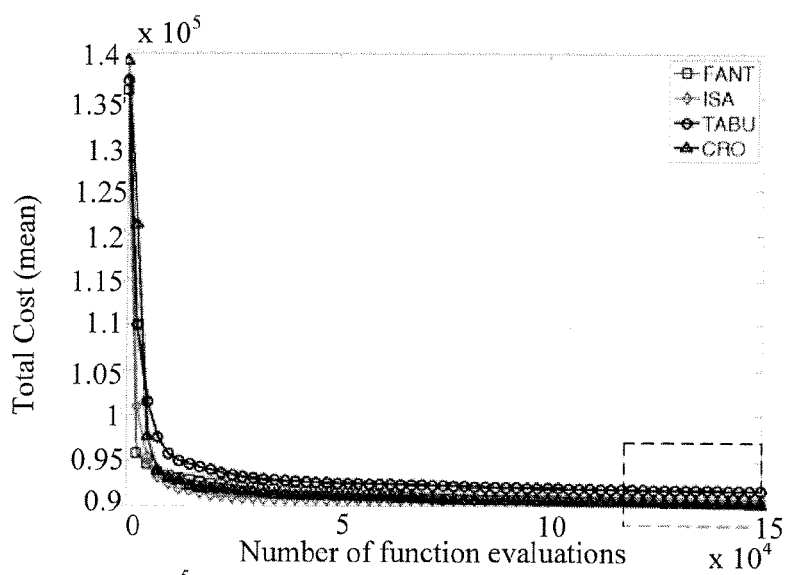
FIG. 3 illustrates several graphs of total cost versus number of evaluations resulting from the application of a particular embodiment of a chemical reaction-type metaheuristic.
Figure 3B:
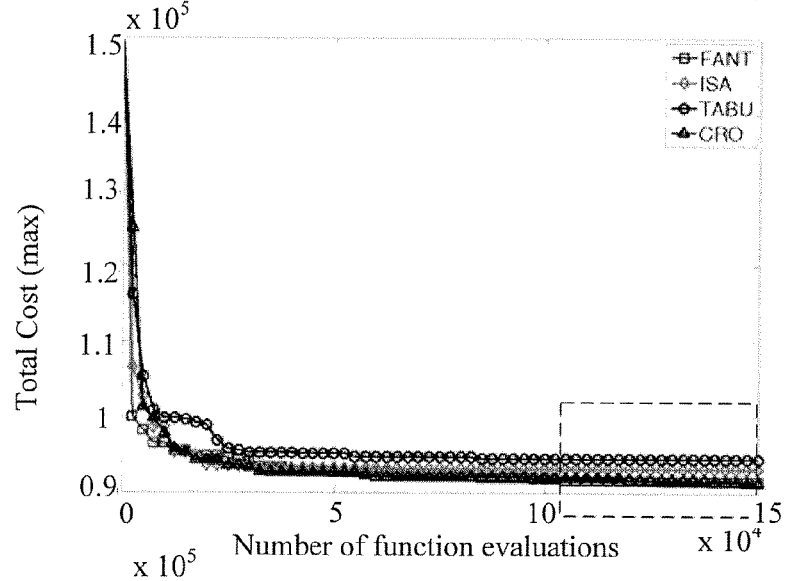
Figure 3C:
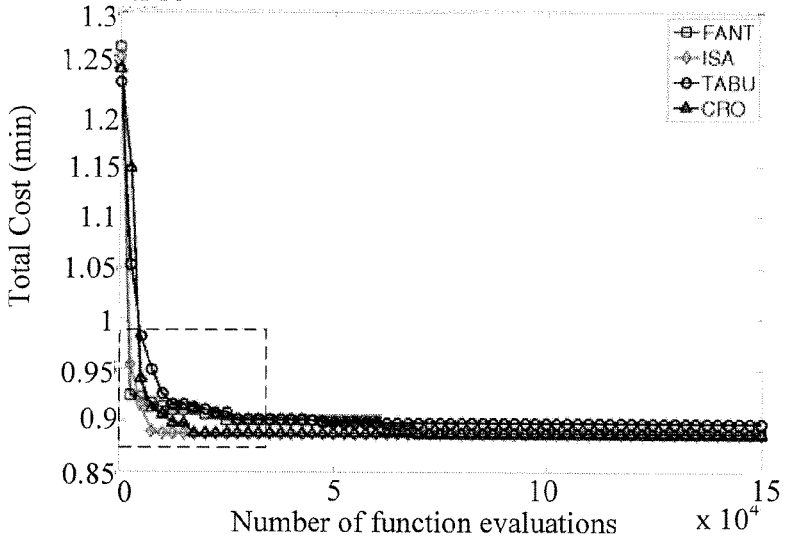
Figure 3D:
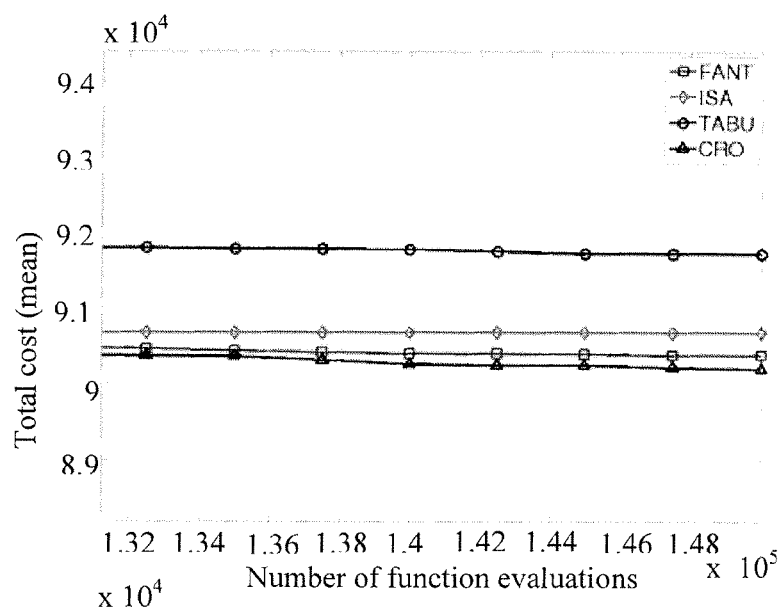
Figure 3E:
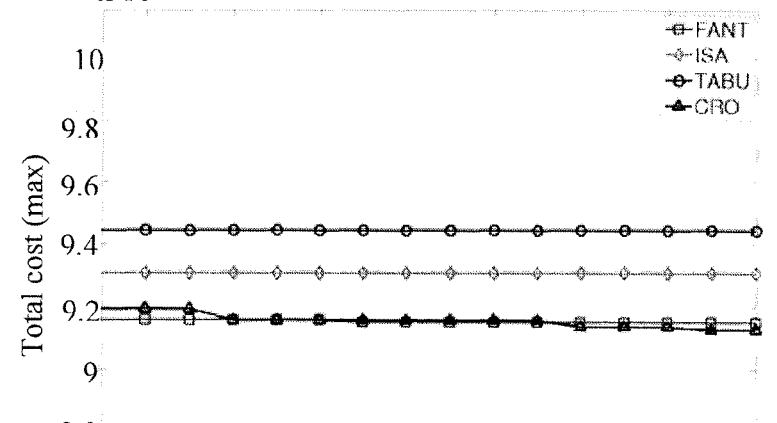
Figure 3F:
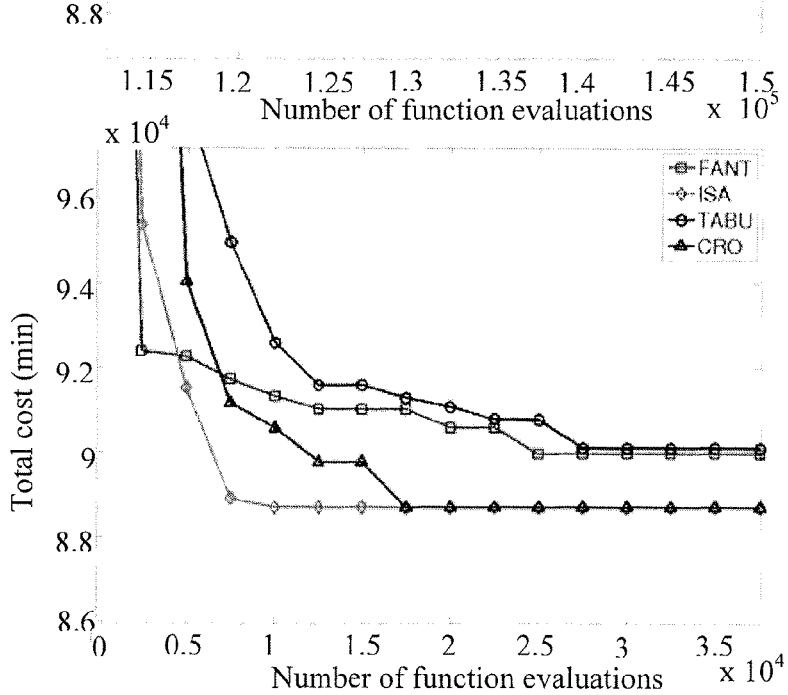

Reference is made in the following detailed description to the accompanying drawings, which form a part of this patent application, wherein like numerals may designate like parts throughout to indicate corresponding or analogous elements. It will be appreciated that for simplicity or clarity of illustration, elements illustrated in the figures have not necessarily been drawn to scale. Further, it is to be understood that other embodiments in addition to those disclosed herein may be utilized and structural or logical changes may be made without departing from the scope of claimed subject matter. Therefore, the scope of claimed subject matter is defined by the appended claims and their equivalents; however, the following detailed description is not to be taken in a limiting sense with respect to such claimed subject matter.

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, methods, apparatuses or systems that would be known by one of ordinary skill have not been described in detail so as not to obscure claimed subject matter.

Reference throughout this specification to "one embodiment" or "an embodiment" may mean that a particular feature, structure, or characteristic described in connection with a particular embodiment may be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described may be combined in various ways in one or more embodiments. In general, of course, these and other issues may vary with the particular context of usage. Therefore, the particular context of the description or the usage of these terms may provide helpful guidance regarding inferences to be drawn for that context.

Likewise, the terms, "and," "and/or," and "or" as used herein may include a variety of meanings that also is expected to depend at least in part upon the context in which such terms are used. Typically, "or" as well as "and/or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, or characteristic in the singular or may be used to describe some combination of features, structures or characteristics. Though, it should be noted that this is merely an illustrative example and claimed subject matter is not limited to this example.

Some portions of the detailed description which follow are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

Metaheuristics are collections of ideas aiming to address general computational problems. A metaheuristic may usually be in the form of a procedure framework which instructs computers how to search for solutions in a solution space for a given computational problem. A metaheuristic typically comprises several building blocks or control parameters for fine tuning. These components may be replaced and/or the parameter values may be changed to suit various situations. At times metaheuristics may involve randomization in the calculation, and thus, results may vary in different runs of the computation. Typically, solutions may not be guaranteed. Thus, metaheuristics may belong to a group of approximation processes. Such metaheuristics may be adopted to address non-deterministic polynomial-time hard (NP-hard) problems because they may locate 'good' solutions relatively efficiently. Metaheuristics may be different from heuristics in that the latter may be tailor-made for specific problems and they may be able to address some problems well but may provide poor solutions to others.

Metaheuristics may apply natural phenomena to address specific problems. Among the most famous ones are Simulated Annealing (SA), Genetic Process (GP), and Ant Colony Process (ACP). SA is inspired by annealing in metallurgy. Annealing refers to a physical process of increasing crystal size of a material and reducing defects through a controllable cooling procedure. By employing the Metropolis process from statistical mechanics, SA allows 'downhill' movements, while 'uphill' movements may be allowed with a probability whose distribution may be controlled at least in part by a so-called temperature parameter. Therefore, it may necessarily reach a local minimum and remain there. As temperature drops, the ability to move from local minima decreases and the system or process converges. GP is based on the idea of natural selection, which is the phenomenon that organisms with favorable characteristics have a higher probability to survive and reproduce than those with unfavorable traits. GP simulates this biological process through producing generations of chromosomes, which represent possible solutions. Through inheritance, selection, and crossover, those chromosomes which are favored by one or more objective functions, and which satisfy specified constraints, survive and 'reproduce' the next generation of chromosomes with higher quality. Moreover, local optima may be bypassed through mutation. ACP mimics ecological behavior of ants in finding food. Food paths represent potential solutions. If ants discover paths to food locations from their colony, they lay down a chemical, called pheromone, along the paths to remind other ants about the food trails. Shorter paths have more pheromone as more ants shuttle around. It employs the effect of evaporation of pheromone to reduce risks associated with local optima. A solution may be obtained by checking the amount of pheromone for the routes.

According to the No-Free-Lunch (NFL) Theorem, all metaheuristics which search for extremes may have the same, substantially the same, or similar performance if averaged over all possible objective functions. By this theorem, no single metaheuristic can always, on the average, surpass the others in performance for all possible problems. But improved performance may still be possible in a particular problem. Thus, in this context, "successful metaheuristics" is intended to refer to those which may be governed by the NFL Theorem, and which may exhibit better performance if applied to some particular types of problems.

As will be discussed in more detail below, a chemical reaction-type metaheuristic may be utilized to address certain types of computational problems. In general, such a chemical reaction-type metaheuristic may exploit the nature of a chemical reaction to move to lower energy states. In science and engineering, many processes and applications involve complex trade-offs in obtaining good solutions. They may at times be formulated as those which cannot be addressed easily. However, if a process or application involves trade-offs in obtaining good solutions, a chemical reaction-type metaheuristic may be applicable.

According to the No-Free-Lunch Theorem, all metaheuristics which search for extremes exhibit similar performance if averaged over all possible problems. So chemical reaction-type metaheuristic may perform comparable to existing metaheuristics if averaged over a large set of problem types. However, as may be demonstrated in various simulations, a chemical reaction-type metaheuristic may outperform some other metaheuristics if applied to the Quadratic Assignment Problem, for example. Therefore, it has the potential to be applied to address certain problems that may be otherwise difficult to solve.

Many problems in everyday life involve resource allocation. Examples include the allocation of communication channels in a wireless network, the scheduling of airplanes to terminals at an airport, etc. A chemical reaction-type metaheuristic may be employed or applied to give an effective allocation, so as to save or reduce the consumption of resources.

Some problems may be so hard that, at best, an approximation of a solution, for example may be made with (meta-)heuristic methods. A metaheuristic, called chemical reaction-type metaheuristic, is disclosed herein which has the potential to be used in addressing these hard problems. Such a chemical reaction-type metaheuristic may mimic the interactions of molecules in a chemical reaction to reach a low energy stable state. Simulation results show that such a chemical reaction-type metaheuristic may be very competitive with the few existing successful metaheuristics and in some instances may outperform such existing successful metaheuristics. Therefore, such a chemical reaction-type metaheuristic may provide an approach for addressing such problems, especially those which may not be adequately addressed with the few generally acknowledged approaches.

Figure 4:
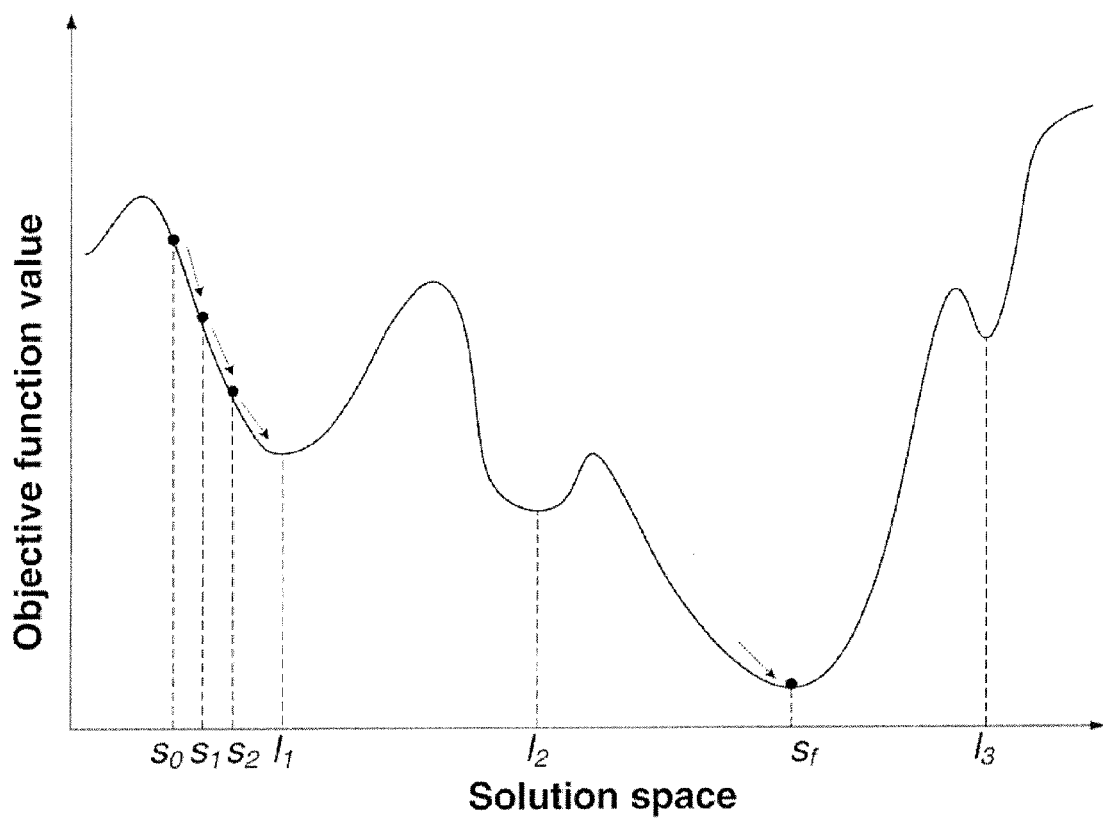
FIG. 4 is a graph illustrating a hypothetical example of applying a metaheuristic.

Trade-offs in obtaining good solutions may be prevalent in many fields of science and engineering, ranging from profit in economics to signal interference in electrical engineering. In daily living, various problems may be encountered, such as finding a desirable route from one place to another, at reduced cost, and reducing the construction costs of building facilities in a city, while, at the same time, reducing congestion of human flow among such facilities. As these examples suggest, without loss of generality, various reduction problems may be considered. For example, there may usually be several points in a region that may offer reduction, just as there may be many valleys in a given terrain. However, as illustrated in FIG. 4, for example, one may globally provide greater reduction than the others. Thus, the others may be viewed as a trap during the search for a good solution, because they appear to provide a solution, whereas a better solution may be available.

Many problems may be formulated into this generic form and the existing methods may be applied to obtain one or more potential solutions with the aid of a computer. However, in computation complexity theory, there is a class of problems, namely, nondeterministic polynomial-time hard (NP-hard) problems, in which no known solution may be found in polynomial time, unless P=NP. In other words, computation efforts grow exponentially with problem size. Such problems may normally not be solvable in a reasonable amount of time or computed results of high quality cannot be guaranteed. Often, the formulated problems may be of huge dimensions and examining every possible solution, referred to as the brute-force method, becomes not feasible. It may take several years of CPU time to obtain solutions even with a state of the art supercomputer, for example. Such long computational time often cannot be tolerated and solution quality may be sacrificed if the processing time is limited. For example, if the time savings is significant and the reduction in solution quality not significant, an acceptable compromise may exist. Thus, approximating processes may be adopted, which may provide "good" solutions efficiently, to tackle NP-hard problems, or the like.

Figure 5:
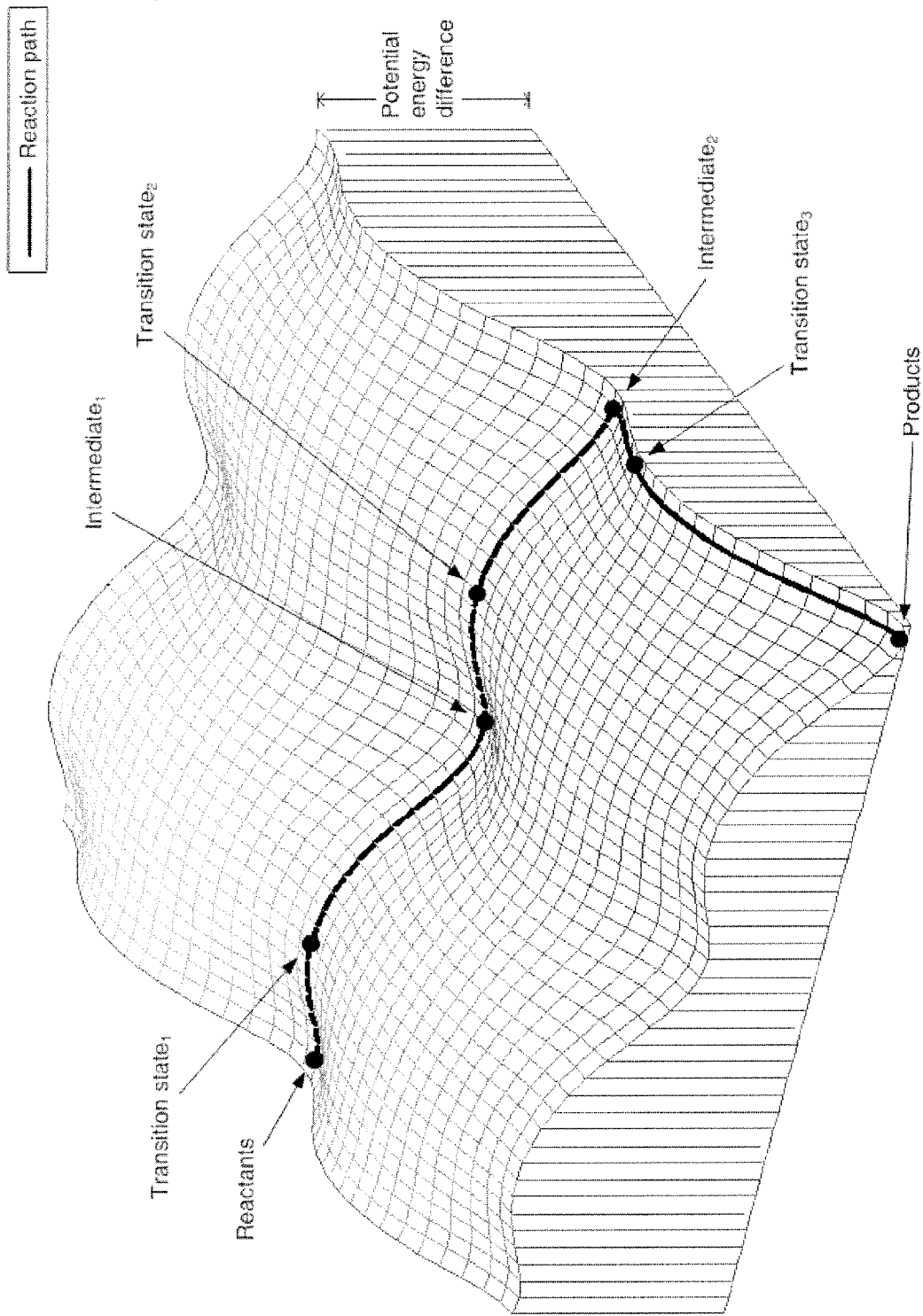
FIG. 5 is a graph illustrating an example of a potential energy surface of a chemical reactive system which may be employed in accordance with one or more embodiments of a chemical-type metaheuristic.

In quantum mechanics and statistical mechanics, chemical reactions and molecular interactions may be modeled with potential energy surfaces (PES) which may be subject to the Born Oppenheimer separation of nuclear and electronic motion. For example, FIG. 5 depicts potential energy (PE) changes of atomic arrangements in one example of a chemical system. One axis represents PE while the rest correspond to atomic positions and possible orientations of involved atomic nuclei. PES may be a two-, three-, or multi-dimensional (hyper) surface, depending at least in part, for example, on the complexity of the chemical system. In any chemical reaction, initial species, e.g. reactants, may change to products by formation and destruction of chemical bonds. Before formation of products, reactants normally may change to a series of intermediate species. These chemical changes may be referred to here as elementary transitions. During a transition, chemicals may be formed in transition states. FIG. 5 is a contour graph illustrating a simple example of a chemical reaction involving three elementary transitions. There is a rule of thumb from observed behavior that reacting systems tend to seek a minimum of free energy. Chemical reactions tend to release energy and, thus, products generally have less energy than reactants. In terms of stability, lower energy substances tend to be more stable. Therefore, products may be more stable than reactants.

Observations regarding chemical reactions may be applied to computation problems. For example, tending toward lower energy relates to finding a global minimum and the process may be viewed as evolving in a stepwise fashion. Thus, one embodiment of a chemical reaction-type metaheuristic may be developed by mimicking what happens to molecules in chemical reactions.

An embodiment of a chemical reaction-type metaheuristic may be arranged to implement the observation that reactions tend to give products with lower energy on a PES. In general, one or more interactions of molecules may be modeled in a chemical reaction to reach a low energy stable state via a chemical reaction-type metaheuristic. Such modeling may be performed via a computing platform that manipulates or transforms electronic signals employed to represent physical electronic or magnetic quantities, or other physical quantities, within the computing platform's memories, registers, or other information storage, transmission, or display devices. FIG. 1, for example, provides an association, for this particular embodiment, between chemical properties of a molecule and computational meaning for this particular embodiment of a metaheuristic. A molecule may be composed of several atoms and may be represented by atom types, bond lengths, angles, or torsions. The term "molecular structure" may be utilized to summarize these characteristics and it may correspond to a computational solution, for this particular embodiment. A change in molecular structure may be tantamount to switching to another solution. According to basic chemistry, a molecule possesses two kinds of energies, potential energy and kinetic energy (KE). The former quantifies the molecular structure in terms of energy and it may be modeled as an objective function value for evaluating a possible solution. The latter may be utilized as a measure of tolerance and may be utilized to obtain a solution with higher function value, since molecules may change structure. Recall that the molecules involved in a reaction attempt to reach the lowest possible potential state, but blindly seeking more favorable structures may result in metastable states, one example being illustrated by a local minimum, perhaps. KE allows molecules to move to a higher potential state and hence present a chance of having a more favorable structure in a future change. Likewise, conservation of energy between PE and KE, within a molecule or among molecules, may occur through some elementary reactions or transitions.

In general, to find a potential for energy reduction, different parts of a PES are explored as much as possible to locate lower point. But normally, a PES may be so large that it may not be feasible to examine every point within a reasonable period of time. Therefore, an intelligent exploration may be made in those parts of a PES where a high possibility of a lower point may reside. The exploration may be implemented with collisions amongst molecules, bringing them towards lower possible energy states through several types of elementary reactions.

For this particular embodiment, there may be two approaches to do the search: intensification and diversification, although claimed subject matter is not limited in scope to this particular embodiment, of course. For a molecule starting at a point on a PES, intensification explores the immediately surrounding area. If a lower energy state cannot be found in this area for some time, diversification results in a jump to a relatively distant area to continue the search. At the same time, a system may try to re-distribute energies among the molecules by inter-changing energies from one to another in different ways.

Figure 7:
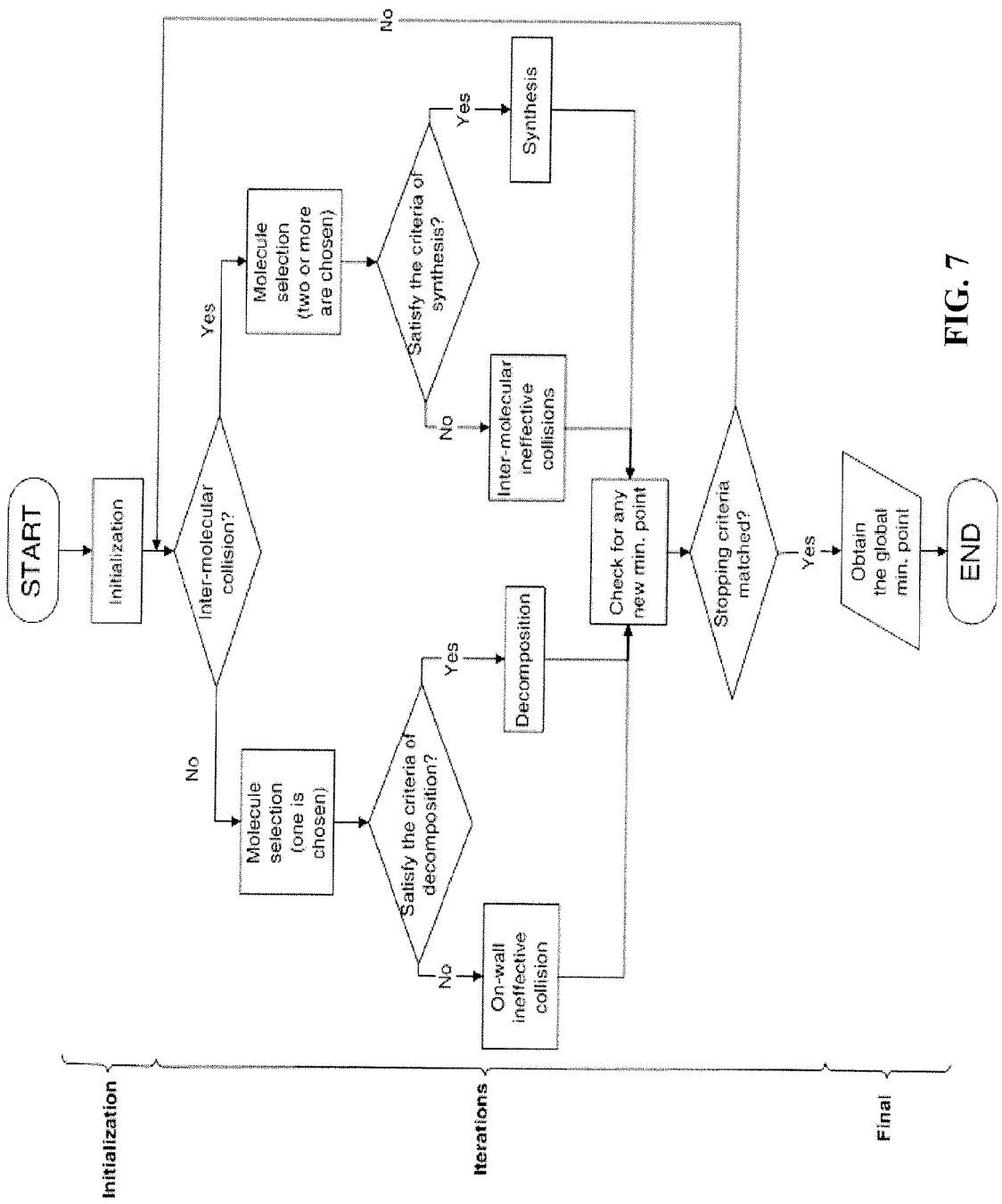
FIG. 7 is a flowchart illustrating a process for implementing an embodiment of a chemical reaction-type metaheuristic.

One embodiment of a process for such a chemical reaction-type metaheuristic will be discussed in greater detail below, and is illustrated in FIG. 7. In such an embodiment, a set of reactant molecules may be initialized by assigning molecular structures randomly and other properties according to problem type. Thus, molecules may be distributed over a PES evenly to reduce the chance of missing an area. Reactant molecules may be put in a closed container. In such a situation, molecules collide either with each other or the walls of the container. Collisions under different conditions provoke distinct elementary reactions, each of which may have a different way of manipulating energies of the involved molecule(s).

For this particular embodiment, one may employ four types of elementary reactions: on-wall ineffective collision, decomposition, inter-molecular ineffective collision, synthesis. These may be categorized in terms of molecularity or extent of change. On-wall ineffective collision and decomposition may comprise unimolecular reactions triggered if a molecule hits a wall of the container, while inter-molecular ineffective collision and synthesis may involve more than one molecule which takes place if molecules collide with each other. On-wall and intermolecular ineffective collisions react much less vigorously than decomposition and synthesis. Ineffective collisions correspond to those cases in which a new molecular structure results in the neighborhood of the molecule on a PES. Conversely, decomposition and synthesis tend to obtain new molecular structures which may be further away from their immediate neighborhood on a PES.

Referring to FIG. 2, item (A) illustrates an on-wall ineffective collision, where a molecule hits the wall and then bounds back. Item (B) illustrates a decomposition, where a molecule hits on the wall and then decomposes into two. Item (C) illustrates an inter-molecular ineffective collision, where two molecules collide with each other and then bounce away. Item (D) illustrates a synthesis, where two molecules collide and combine together. The figure shows both (C) and (D) involving two molecules but more may be added, depending on the implementation. With respect to molecularity, (A) and (B) belong to one class while (C) and (D) belong to another. With respect to extent of change, (A) and (C) belong to one group while (B) and (D) pertain to another.

Collisions trigger different types of elementary reactions depending at least in part on the underlying conditions. Change of energy in these events may be examined. With time, molecules "explore" different parts of a PES and elementary reactions bring them towards lower energy states. If a molecule assumes a new molecular structure with lower PE than those before, it may be recorded. The process may stop once a stopping criterion is reached. The appropriate stopping criteria may be determined, depending at least in part on problem type. A solution obtained in a run of a chemical reaction-type metaheuristic may be the structure whose PE is lower than the others during the whole course of the reaction.

Simulations may be utilized to show that an embodiment of a chemical reaction-type metaheuristic may be a successful metaheuristic. For example, such an embodiment may be applied to the quadratic assignment problem (QAP). QAP may be relatively easy to state but may be one of the more difficult NP-hard combinatorial problems. For example, an instance of problems in which size is larger than 20 are generally considered intractable. An embodiment of a chemical reaction-type metaheuristic may be applied to address a QAP type NP-hard problem. For example, an embodiment of a chemical reaction-type metaheuristic may be applied to address a real world electronic component placement problem. Such as the electronic component placement problem described in Miranda, Luna, Mateus and Ferreira, "A performance guarantee heuristic for electronic components placement problems including thermal effects," *Computers & Operations Research*, Volume 32, Issue 11, November 2005, Pages 2937-2957, and/or the electronic component placement problem described in Duman and Or, "The quadratic assignment problem in the context of the printed circuit board assembly process," *Computers & Operations Research*, Volume 34, Issue 1, January 2007, Pages 163-179. Additionally or alternatively, an embodiment of a chemical reaction-type metaheuristic may be applied to address other real world problems. For example, an embodiment of a chemical reaction-type metaheuristic may be applied to address allocating channels in radio network, as described in U.S. Pat. No. 5,778,317; assigning sensor reports in tracking with sensors, as described in U.S. Pat. No. 6,055,523; cell placement for integrated circuit chip, as described in U.S. Pat. No. 5,796,625; and/or circuit designing, as described in U.S. Pat. No. 5,897,628; and/or the like.

QAP tries to reduce total cost from assigning facilities to locations. The facilities may be of different types and the number of facilities and the number of locations must be equal, for this particular embodiment. Given the distance between a pair of locations and the human flow between any two facilities, the cost is, for this particular embodiment, defined as (flow×distance), and the total cost is obtained by summing the cost of any possible pairs of facilities and locations. Each type of facility is built at a unique location. In other words, duplicate facilities cannot be assigned to distinct locations and each location must have a facility assigned. In fact, this constraint makes the problem hard to address. Moreover, the number of possible solutions grows exponentially with the problem dimensions (here, n). Most applications have n larger than 20, which is beyond the size of computational tractability, and thus, a brute-force method may be fruitless. Different QAP instances may have different n, flow, and distance values.

The effectiveness of an embodiment of a chemical reaction-type metaheuristic may be evaluated using the instance KRA32 taken from a QAP digital library. KRA32 refers to an instance of QAP that defines distance and flow information with real-world data originally used to plan Klinikum Regensburg in Germany. A run of simulations may be terminated once the number of evaluations reaches 150,000. The results of this simulation using an embodiment of the chemical reaction-type metaheuristic (labeled as CRO) may be compared with three other metaheuristics, here, FANT, ISA and TABU (see Table 1). FANT, ISA and TABU refer to metaheuristics derived from Ant Colony Process (ACP), Simulated Annealing (SA), and Taboo search, respectively, and have been adapted for use in solving QAP. In the simulations discussed below, the particular embodiment of a chemical reaction-type metaheuristic described above outperformed these particular metaheuristics, in terms of the mean, maximum, and minimum costs obtained. As illustrated in FIG. 3, the results may be plotted versus the number of evaluations in the period of a simulation run. This embodiment obtains better or equally good results.

The performance for this particular embodiment may be compared with those of FANT, ISA and TABU, and recording result after an interval of 2,500 function evaluations. In FIG. 3, (A) illustrates a plot of mean cost, (B) illustrates a plot of maximum cost, and (C) illustrates a plot of minimum cost. For easier observation, (D), (E) and (F) show more detailed portions of the graphs on their left, corresponding to the dotted-line boxes.

As discussed above, this particular embodiment may be guided by the transformation of molecules along a PES towards a more stable state by redistributing energies among molecules and by inter-changing energies from one form to another. As shown by the previous discussion, this particular embodiment of a chemical reaction-type metaheuristic may be applied to address a QAP type NP-hard problem. Thus, this particular embodiment provides the same, substantially the same, or similar performance as the others on average but outperform other metaheuristics if matched to the appropriate problem type.

Other embodiments of chemical reaction-type metaheuristics may be provided, such as, for example through hybridation with other metaheuristics or through incorporation of so-called greedy approaches.

Besides KRA32, the effectiveness of an embodiment of a chemical reaction-type metaheuristic may also be evaluated using 23 instances from the same QAP digital library. Referring to Table 1 below, simulation results may be compared with three other metaheuristics. Under each metaheuristic, the three columns show "Min,", "Max," and "Mean" representing the best case, the worst case, and the average respectively, in 50 runs. Results from different runs vary from randomization in the calculations. Figures in brackets indicate the best metaheuristic result. On average, the chemical reaction-type metaheuristic performs best.

TABLE 1

| Instance | Problem size | Global min. | Function evaluation limit | FANT | | | ISA |
|---|---|---|---|---|---|---|---|
| | | | | Min. | Max. | Mean | Min. |
| nug21 | 21 | 2438 | 150 000 | (2438) | 2464 | 2444.44 | (2438) |
| nug22 | 22 | 3596 | 150 000 | (3596) | 3632 | 3599.80 | (3596) |
| nug24 | 24 | 3488 | 150 000 | (3488) | 3546 | 3500.40 | (3488) |
| nug25 | 25 | 3744 | 150 000 | (3744) | 3772 | 3750.36 | (3744) |
| nug27 | 27 | 5234 | 150 000 | (5234) | 5324 | (5249.52) | (5234) |
| nug28 | 28 | 5166 | 150 000 | (5166) | 5266 | 5203.24 | (5166) |
| nug30 | 30 | 6124 | 150 000 | 6128 | 6210 | 6158.56 | (6124) |
| kra30a | 30 | 88 900 | 150 000 | (88 900) | 93 200 | (90 601.80) | 90 160 |
| kra30b | 30 | 91 420 | 150 000 | (91 420) | 93 010 | 92 031.00 | 91 590 |
| kra32 | 32 | 88 700 | 150 000 | (88 700) | 91 490 | 90 373.80 | (88 700) |
| tai10b | 10 | 1 183 760 | 50 000 | (1 183 760) | (1 183 760) | (1 183 760.00) | (1 183 760) |
| tai12b | 12 | 39 464 925 | 50 000 | (39 464 925) | (39 464 925) | (39 464 925.00) | (39 464 925) |
| tai15b | 15 | 51 765 268 | 50 000 | (51 765 268) | (51 855 477) | (51 774 385.84) | (51 765 268) |
| esc32a | 32 | 130 | 150 000 | (130) | 146 | 138.60 | 134 |
| esc32b | 32 | 168 | 150 000 | (168) | (192) | 178.88 | 188 |
| esc32c | 32 | 642 | 150 000 | (642) | (642) | (642.00) | (642) |
| esc32d | 32 | 200 | 150 000 | (200) | (200) | (200.00) | (200) |
| esc32e | 32 | 2 | 150 000 | (2) | (2) | (2.00) | (2) |
| esc32g | 32 | 6 | 150 000 | (6) | (6) | (6.00) | (6) |
| esc32h | 32 | 438 | 150 000 | (438) | 440 | 438.12 | (438) |
| tai64c | 64 | 1 855 928 | 150 000 | (1 855 928) | (1 857 646) | (1 856 255.96) | (1 855 928) |
| wil50 | 50 | 48 816 | 150 000 | 48 964 | 49 254 | 49 098.72 | (48 844) |
| wil100 | 100 | 273 038 | 150 000 | 274 800 | (275 980) | 275 436.48 | (273 816) |

| Instance | ISA | | TABU | | | CRO |
|---|---|---|---|---|---|---|
| | Max. | Mean | Min. | Max. | Mean | Min. |
| nug21 | 2462 | 2445.72 | (2438) | 2484 | 2452.28 | (2438) |
| nug22 | 3644 | 3607.84 | (3596) | 3696 | 3618.92 | (3596) |
| nug24 | (3526) | 3498.40 | (3488) | 3554 | 3503.20 | (3488) |
| nug25 | 3768 | (3746.96) | (3744) | 3788 | 3751.76 | (3744) |
| nug27 | 5314 | 5259.04 | (5234) | 5382 | 5285.56 | (5234) |
| nug28 | 5278 | (5201.28) | (5166) | 5282 | 5219.76 | (5166) |
| nug30 | 6214 | (6146.96) | (6124) | 6234 | 6175.28 | 6128 |
| kra30a | 94 340 | 91 664.20 | (88 900) | 95 280 | 92428.40 | (88 900) |
| kra30b | 94 990 | 92 752 | 91 490 | 96 050 | 93029.60 | 91 490 |
| kra32 | 93 060 | 90 664.60 | (88 700) | 94 430 | 91714.60 | (88 700) |
| tai10b | 1 213 671 | 1 184 925.80 | (1 183 760) | (1 183 760) | (1 183 760.00) | (1 183 760) |
| tai12b | 45 097 713 | 41 801 386.02 | (39 464 925) | 40 063 583 | 39 526 972.08 | (3 9464 925) |
| tai15b | 52 035 184 | 51 814 064.70 | (51 765 268) | 51 944 836 | 51 822 408.02 | (51765268) |
| esc32a | 150 | 140.60 | 134 | 162 | 145.80 | (130) |
| esc32b | 224 | 208.96 | 168 | 224 | 196.32 | (168) |
| esc32c | (642) | (642.00) | (642) | 646 | 642.24 | (642) |
| esc32d | 208 | 202.44 | (200) | 216 | 205.32 | (200) |
| esc32e | (2) | (2.00) | (2) | (2) | (2.00) | (2) |
| esc32g | (6) | (6.00) | (6) | (6) | (6.00) | (6) |
| esc32h | 442 | 439.80 | 440 | 478 | 453.00 | (438) |
| tai64c | 1 857 660 | 1 859 213.60 | (1 855 928) | 1 883 516 | 1 863 245.04 | (1 855 928) |
| wil50 | 49 296 | (48 937.12) | 48 996 | 49 828 | 49 343.88 | 48 918 |
| wil100 | 276 034 | (274 683.32) | 280 634 | 283 190 | 281 779.56 | 274 618 |

| Instance | CRO | | |
|---|---|---|---|
| | Max. | Mean | Computational time (s) |
| nug21 | (2456) | (2443.64) | 1.046 |
| nug22 | (3606) | (3597.80) | 1.109 |
| nug24 | (3526) | (3494.88) | 1.265 |
| nug25 | (3760) | 3749.68 | 1.343 |
| nug27 | (5298) | 5259.36 | 1.500 |
| nug28 | (5238) | 5202.52 | 1.610 |
| nug30 | (6206) | 6170.12 | 1.781 |
| kra30a | (91 800) | 90 664.20 | 1.797 |
| kra30b | (92 840) | (92 022.80) | 1.797 |
| kra32 | (91 260) | (90 190.80) | 1.984 |
| tai10b | 1 187 126 | 1 184 029.28 | 0.407 |
| tai12b | 40 063 573 | 3 911 175.94 | 0.485 |
| tai15b | 52 205 386 | 52 035 537.10 | 0.640 |

TABLE 1-continued

| | | | |
|---|---|---|---|
| esc32a | (142) | (136.84) | 2.000 |
| esc32b | (192) | (175.36) | 1.985 |
| esc32c | (642) | (642.00) | 2.016 |
| esc32d | (200) | (200.00) | 2.015 |
| esc32e | (2) | (2.00) | 2.031 |
| esc32g | (6) | (6.00) | 2.016 |
| esc32h | (438) | (438.00) | 2.000 |
| tai64c | 1 860 348 | 1 856 796.04 | 6.984 |
| wil50 | (49 214) | 49 071.12 | 4.407 |
| wil100 | 276 278 | 275 291.16 | 15.985 |

There may be three stages in an embodiment of a chemical reaction-type metaheuristic: initialization, iteration and final stage. FIG. 7 shows an example chemical reaction-type metaheuristic in accordance with one or more embodiments, although the scope of claimed subject matter is not limited in this respect. Additionally, although the embodiment chemical reaction-type metaheuristic, as shown in FIG. 7, comprises one particular order, this order does not necessarily limit claimed subject matter to any particular order. Likewise, intervening or additional blocks not shown in FIG. 7 may be employed or blocks shown in FIG. 7 may be eliminated, without departing from the scope of claimed subject matter. The embodiment of a chemical reaction-type metaheuristic, as shown in FIG. 7 may in alternative embodiments be implemented in software, hardware, or firmware, and may comprise discrete operations.

In initialization, the solution space and some functions may be defined, and values may be assigned to several variables and control parameters. Such an embodiment may comprise a population-based metaheuristic and may handle more than one solution from an iteration. But the number of solutions held in memory may be subject to change, depending, for example, at least in part on the effects of decomposition and synthesis. Table 2, listed below, shows an example of symbols used in this particular embodiment of a chemical reaction-type metaheuristic. First, Pop may be produced by generating PopSize number of solutions randomly in the solution space. This may increase the scope of searching over ObjFunc( ). In an iteration stage, a number of iterations may be performed. In one iteration, a collision may be chosen. First, a decision may be made whether it is a unimolecular or an intermolecular collision. To do this, a random number p may be generated, in the interval of [0, 1]. If p is larger than MoleColl, it may result in an event of unimolecular collision. Otherwise, an inter-molecular collision may take place. Also, a unimolecular collision may be present if there remains one molecule in Pop. A suitable number of molecules may be randomly selected from Pop, for example, according to a just-decided collision type. Molecules involved in a collision may depend at least in part on their locations in the container. However, this observation may be ignored in this embodiment for simplicity. Next, the criteria of decomposition or synthesis may be examined to determine type of collision. A point found may be checked for reduction in energy and recorded. This iteration stage may repeat until a stopping criterion is reached. For example, a stopping criterion may be defined based at least in part on the amount of CPU time used, the number of iterations performed, an objective function value less than a predefined threshold, the number of iterations performed without an improvement or any other appropriate criteria. In a final state, the solution with the lowest value found over ObjFunc( ) may be provided.

Figure 8:
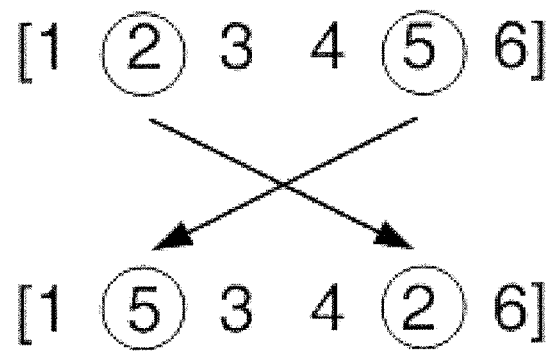
FIG. 8 illustrates an example of neighbors in a two-exchange neighborhood structure.

Table 3 shows values assigned to control parameters of this embodiment of a chemical reaction-type metaheuristic used in the simulation. A possible solution may be in the form of permutation of problem dimensions, such as if QAP is being solved, for example. FIG. 8 shows two possible solutions if problem dimension is six. As illustrated by FIG. 8, a two-exchange neighborhood structure may be adopted since there may be no natural neighborhood structure defined for permutations, as compared with continuous functions. Suppose a current solution is $\omega$ and an attempt is made to perform a move to $\omega'$ in its neighborhood. In an on-wall ineffective collision, a move may be allowed if $$PE_\omega + KE_\omega \geq PE_{\omega'} \quad (1)$$

where $PE_{\omega'}$ may be calculated by putting $\omega'$ into ObjFunc( ). We get $KE_{\omega'} = (PE_\omega + KE_\omega - PE_{\omega'}) \times q$ where $q \in [KELossRate, 1]$, where $(1-q)$ represents a fraction of KE lost to the environment from hitting a wall. Lost energy may be stored up in an energy pool. If inequality (1) does not hold, a move may be prohibited.

Similarly in inter-molecular ineffective collision, two new solutions $\omega_1'$ and $\omega_2'$ may be obtained from the neighborhoods of $\omega_1$ and $\omega_2$ respectively. A change may be accepted if:

$$PE_{\omega_1} + PE_{\omega_2} + KE_{\omega_1} + KE_{\omega_2} \geq PE_{\omega_1'} + PE_{\omega_2'} \quad (2)$$

Let Buffer=$(PE_{\omega_1} + PE_{\omega_2} + KE_{\omega_1} + KE_{\omega_2}) - (PE_{\omega_1'} + PE_{\omega_2'})$, then $KE_{\omega_1'} = \text{Buffer} \times k$ and $KE_{\omega_2'} = \text{Buffer} \times (1-k)$ may be obtained, where k may be a random number generated from the interval [0, 1]. Likewise, $\omega_1$ and $\omega_2$ may not change to $\omega_1'$ and $\omega_2'$ respectively if inequality (2) fails.

Figure 9:
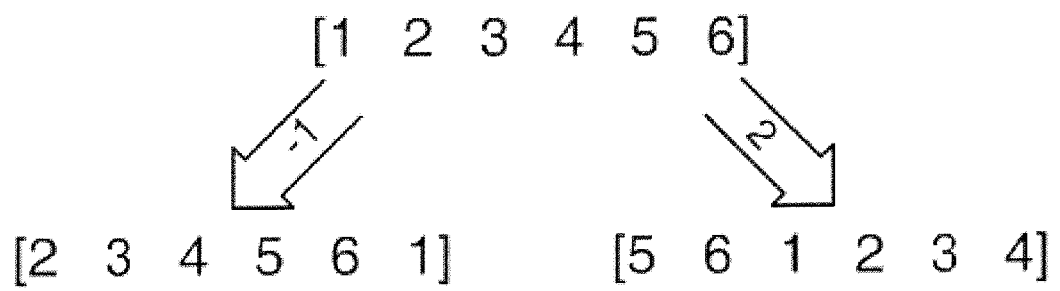
FIG. 9 illustrates two examples of applying a circular shift operator in accordance with one or more embodiments.

In decomposition, two solutions $\omega_1'$ and $\omega_2'$ may be obtained from $\omega$. A circular shift operator may be adopted, such as illustrated at FIG. 9, for example, to generate new solutions, although claimed subject matter is not limited in scope to this particular approach. Decomposition may be triggered if a selected molecule has stayed in a stable state for a certain period of time. For example, if (number of hits−minimum hit number)>$\alpha$, a molecule has not moved to a lower energy state for a certain time in terms of number of hits $\alpha$. Stored energy from energy pool accumulation due to on wall ineffective collisions may compensate if total energy of an original molecule with solution $\omega$ is not enough to support a change.

In synthesis, an attempt may be made to generate a new solution $\omega'$ from two existing solutions, $\omega_1$ and $\omega_2$, by using a distance-preserving crossover operator. It may be triggered if both molecules have insufficient KEs. For example, if $KE_1 \leq \beta$ and $KE_2 \leq \beta$, where $\beta$ defines the least amount of KE a molecule may possess. $\omega'$ may be accepted if $$PE_{\omega_1} + PE_{\omega_2} + KE_{\omega_1} + KE_{\omega_2} \geq PE_{\omega'} \quad (3)$$

We get $KE_{\omega'} = PE_{\omega_1} + PE_{\omega_2} + KE_{\omega_1} + KE_{\omega_2} - PE_{\omega'}$. Thus, $\omega_1$ and $\omega_2$ may be retained instead of $\omega_1'$ if inequality (3) does not hold. Inequalities (1-3) reflect conservation of energy. Simulated versions of these four elementary reactions may be summarized in terms of intensification and diversification in Table 4, as illustrated below.

Values of parameters, neighborhood structure, conditions for triggering decomposition and synthesis, circular shift and distance-preserving crossover operators may in alternate embodiments be tuned to match problem type.

The quadratic assignment problem (QAP) may be defined, as described below. Consider a problem of size n. There may be n facilities to be assigned to n locations. $f_{ij}$ may be defined as the flow between facilities i and j, and $d_{kl}$ as the distance between locations k and l. An objective function and constraints may be written as follows:

$$\min \sum_{i,j=1}^{n} \sum_{k,l=1}^{n} f_{ij} d_{kl} x_{ik} x_{jl}$$

subject to $$\sum_{i=1}^{n} x_{ij} = 1 \quad 1 \le j \le n,$$

$$\sum_{j=1}^{n} x_{ij} = 1 \quad 1 \le i \le n,$$

$$x_{ij} \in \{0, 1\} \quad 1 \le i, j \le n$$

If the constraints are examined more carefully, it may be found that possible solutions may be in the form of permutation of n elements. Positions and values of the permutation may correspond to locations and facilities, respectively. Then the objective function value may be determined by summing the products of flow and distance of possible pairs in the permutation. Consider an instance of the problem with n equal four. One possible solution is [2, 4, 3, 1], with facility 2 assigned to location 1, facility 4 to location 2, etc. This solution may be evaluated by computing:

$f_{22}d_{11}+f_{24}d_{12}+f_{23}d_{13}+f_{21}d_{14}+$ $f_{42}d_{21}+f_{44}d_{22}+f_{43}d_{23}+f_{41}d_{24}+$ $f_{32}d_{31}+f_{34}d_{32}+f_{33}d_{33}+f_{31}d_{34}+$ $f_{12}d_{41}+f_{14}d_{42}+f_{13}d_{43}+f_{11}d_{44}.$

Referring to FIG. 5, the z-axis represents potential energy difference. It characterizes how energy changes during a reaction. The x- and y-axes capture molecular structures of chemical substances. The solid line gives reaction pathway from reactants to products, via several transition states and an intermediate species.

Figure 6:
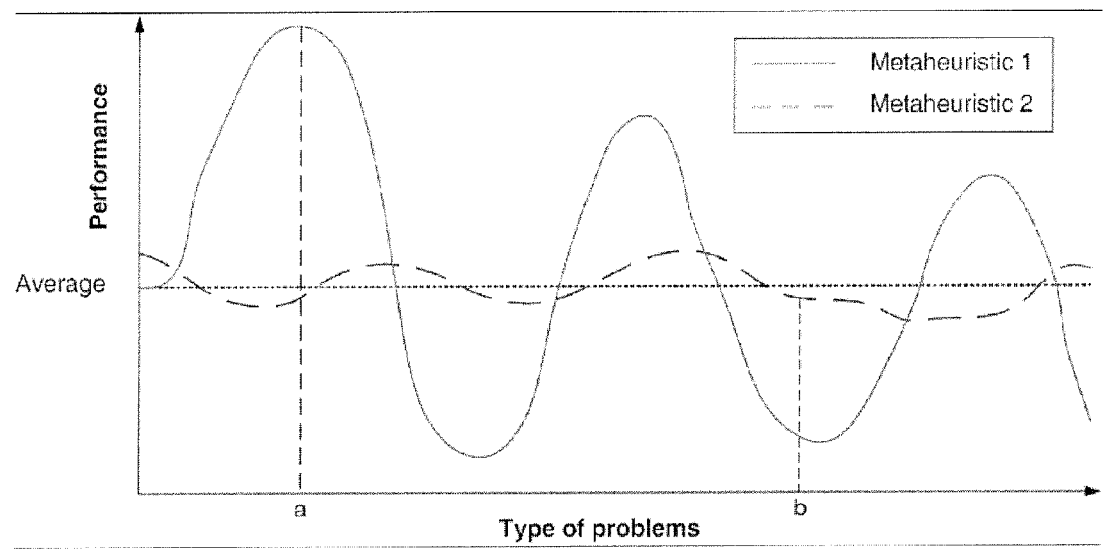
FIG. 6 is a graph illustrating a comparison of performance for different problem types from applying different metaheuristics.

FIG. 6 illustrates that metaheuristics have similar performance on the average. However, one may have superior performance for some types of problems but becomes inferior on other problems. At point (a), metaheuristic 1 outperforms metaheuristic 2, but at point (b), metaheuristic 2 outperforms metaheuristic 1.

FIG. 7 is a flowchart illustrating a particular metaheuristic embodiment. START and END indicate beginning and termination, respectively, of a run for this particular embodiment. A run may start with initialization, perform a certain number of iterations, and terminate at a final stage.

FIG. 8 provides an example of neighbors in a two-exchange neighborhood structure. The 1st permutation means the 1st facility may be assigned to location 1, the 2nd facility to location 2 and so forth. A neighbor may be defined by exchanging values of any two positions. The 2nd permutation gives a neighbor of the 1st. In this representation, the 5th facility may be assigned to location 2 and the $2^{nd}$ facility to location 5.

FIG. 9 illustrates two examples of a circular shift operator. A new solution may be obtained by generating an integer in the range of [−n, n] where n is the size of the permutation, indicating how many transitions may be utilized to shift from the original one. Negative and positive values mean shifting to the left and right, respectively. The left permutation may be obtained by shifting to the left for one transition, while the right one may be obtained by shifting to the right for two transitions.

Referring to Table 2 below, variables and parameters used in this embodiment of a chemical reaction-type metaheuristic are provided. The second column shows symbols of functions, variables and parameters. The third and fourth columns give computational and chemical meanings, respectively.

TABLE 2

| Type | Symbol | Algorithmic meaning | Chemical meaning |
|---|---|---|---|
| Function | ObjFunc( ) | Objective function | Function defining PES |
|  | Neighbor( ) | Neighbor candidate generator | Neighborhood structure on PES |
| Variable | Nvars | Number of variables representing a solution; dimensions of the problem | Total number of characteristics of a molecule |
|  | Pop | Set of solutions; 2-D matrix where each row carries the values of a solution | Set of molecules |
|  | PE | Vector of objective function values; PE = ObjFunc(Pop) | Potential energy of all the molecules |
|  | KE | Vector of number measuring the tolerance of the solutions to have worse objective function values afterwards | Kinetic energy of all the molecules |
| Parameter | PopSize | Number of solutions maintained; number of rows in Pop | Number of molecules in the container |
|  | KELossRate | Percentage upper limit of reduction of KE in on-wall ineffective collisions | Percentage upper limit of KE lost to the environment in on-wall ineffective collisions |
|  | MoleColl | Fraction of all elementary reactions corresponding to inter-molecular reactions | Same as the algorithmic meaning |
|  | InitialKE | Initial value assigned to each element of KE in the initialization stage | KE of the initial set of molecules |

Referring to Table 3 below, values may be assigned to control parameters. For example, α and β refer to thresholds defined for conditions for decomposition and synthesis, respectively.

TABLE 3

| Parameter | Value |
| --- | --- |
| PopSize | 25 |
| KELossRate | 0.8 |
| MoleColl | 0.2 |
| InitialKE | 1 000 000 |
| $\alpha^a$ | 1300 |
| $\beta^a$ | 10 000 |

Referring to Table 4 below, intensification and diversification of four elementary reactions is illustrated. More ticks indicate stronger effects. Note that a distance-preserving crossover operator used in synthesis has some effect of intensification. The extent of intensification and diversification may vary, depending at least in part, for example, on the particular implementation of the elementary reactions in the simulation.

TABLE 4

| Elementary reactions | Intensification | Diversification |
| --- | --- | --- |
| On-wall ineffective collision | ✓✓ | ✓ |
| Decomposition | | ✓✓ |
| Intermolecular collision | ✓✓ | ✓ |
| Synthesis | ✓ | ✓✓ |

It will, of course, be understood that, although particular embodiments have just been described, claimed subject matter is not limited in scope to a particular embodiment or implementation. For example, one embodiment may be in hardware, such as implemented to operate on a device or combination of devices, for example, whereas another embodiment may be in software. Likewise, an embodiment may be implemented in firmware or as any combination of hardware, software, or firmware, for example. Likewise, although claimed subject matter is not limited in scope in this respect, one embodiment may comprise one or more articles, such as a storage medium or storage media. This storage media, such as, one or more CD-ROMs or disks, for example, may have stored thereon instructions, that if executed by a system, such as a computer system, computing platform, or other system, for example, may enable an embodiment in accordance with claimed subject matter to be executed, such as one of the embodiments previously described, for example. As one potential example, a computing platform may include: one or more processing units or processors; one or more input/output devices, such as a display, a keyboard, or a mouse; one or more memories, such as static random access memory, dynamic random access memory, flash memory or a hard drive, although, again, claimed subject matter is not limited in scope to this example.

Some portions of the detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

In one implementation, one or more interactions of molecules may be modeled in a chemical reaction to reach a low energy stable state via a chemical reaction-type metaheuristic. Such modeling may be performed via a computing platform that manipulates or transforms electronic signals employed to represent physical electronic or magnetic quantities, or other physical quantities, within the computing platform's memories, registers, or other information storage, transmission, or display devices.

For example, a computing platform may be adapted to execute instructions so that one or more interactions of molecules in a chemical reaction may be represented within such a computing platform by digital electronic signals. Such interactions may be represented within such a computing platform by so as to reach a low energy stable state via digital electronic signal implementation of a chemical reaction-type metaheuristic. Additionally or alternatively, such a computing platform may be adapted to implement elementary reactions. For example, one or more of the following types of elementary reactions may be implemented: on-wall ineffective collision; decomposition; inter-molecular ineffective collision; or synthesis. Such elementary reactions may be implemented so that one or more interactions of molecules in a chemical reaction represented within such a computing platform by digital electronic signals may reach a low energy stable state via digital-electronic signal implementation of such a chemical reaction-type metaheuristic. Additionally or alternatively, such a computing platform may be adapted to utilize digital electronic signals to process one or more outcomes for a non-deterministic polynomial-time hard (NP-hard) problem, and/or the like.

Similarly, a computing platform may be adapted to perform digital electronic signal implementation of a chemical reaction-type metaheuristic. In such a digital electronic signal implementation, digital electronic signals may represent one or more interactions of molecules in a chemical reaction to reach a low energy stable state. Such a computing platform may also be adapted to apply a digital electronic process to obtain one or more outcomes for an objective function subject to constraints via such a digital electronic signal implementation of a chemical reaction-type metaheuristic. Additionally or alternatively, a computing platform may be adapted to apply a digital electronic process to obtain one or more outcomes for an objective function subject to constraints that includes an otherwise computationally intractable problem. In such a case, such an objective function that includes an otherwise computationally intractable problem may be processed via a digital electronic signal implementation of a chemical reaction-type metaheuristic to obtain one or more outcomes. Additionally or alternatively, a computing platform may be adapted to apply a digital electronic process to obtain one or more outcomes for an objective function subject to constraints, where such outcomes may include improved outcomes relative to those obtainable from alternative metaheuristics. For example, such outcomes may include improved outcomes relative to those obtainable from, instead, implementing at least one of the following metaheuristics: Simulated Annealing (SA), Genetic Process (GP), or Ant Colony Process (ACP), and/or the like.

In the preceding description, various aspects of claimed subject matter have been described. For purposes of explanation, specific numbers, systems or configurations were set forth to provide a thorough understanding of claimed subject matter. However, it should be apparent to one skilled in the art having the benefit of this disclosure that claimed subject matter may be practiced without these specific details. In other instances, features that would be understood by one of ordinary skill were omitted or simplified so as not to obscure claimed subject matter. While certain features have been illustrated or described herein, many modifications, substitutions, changes or equivalents will now occur to those skilled in the art. It is, therefore, to be understood that the appended claims are intended to cover all such modifications or changes as fall within the true spirit of claimed subject matter.

What is claimed is:

1. An apparatus comprising:
   one or more processors configured to:
   obtain an objective function that is subject to constraints and a number of possible solutions to the objective function;
   assign molecular structures and chemical reaction parameters to a plurality of reactant molecules, wherein the molecular structures comprise a kinetic energy value, a potential energy value, an atomic position, and an orientation;
   model a plurality of reactions involving one or more of the molecular structures, wherein the plurality of reactions comprise at least one of an on-wall ineffective collision, a decomposition, an inter-molecular ineffective collision, and a synthesis, wherein to select each reaction in the plurality of reactions one or more processors configured to:
   determine a random number;
   determine if the random number is less than an inter-molecular reaction parameter;
   model an on-wall ineffective collision of a molecular structure;
   determine if a sum of the potential energy value and kinetic energy value of the molecular structure is greater than a new potential energy value of the molecular structure after the on-wall ineffective collision based upon a determination that the random number is less than the inter-molecular reaction parameter;
   allow the on-wall ineffective collision based upon a determination that the sum is greater than the new potential energy;
   determine the molecular structure has stayed in a stable state for at least a predetermined period of time based upon the determination that the sum is less than the new potential energy value;
   decompose the molecular structure into two or more molecular structures based upon the determination that the molecular structure has stayed in the stable state for at least the predetermined period of time; and
   model an inter-molecular collision based upon a determination that the random number is greater than the inter-molecular reaction parameter, wherein the inter-molecular collision is a synthesis or an inter-molecular ineffective collision;
   determine, after each of the plurality of reactions, an energy value of the molecular structures based upon the potential energy values and kinetic energy values of the molecular structures;
   store the molecular structures when the energy value is less than a previously stored energy value;
   determine a stopping criteria is met; and
   determine the solution for the objective function as the stored molecular structures that has the lowest energy value that corresponds to the global minimum.

2. The apparatus of claim 1, wherein the objective function comprises a non-deterministic polynomial-time hard (NP-hard) problem.

3. A method comprising:
   obtaining an objective function that is subject to constraints and a number of possible solutions to the objective function;
   assigning molecular structures and chemical reaction parameters to a plurality of reactant molecules, wherein the molecular structures comprise a kinetic energy value, a potential energy value, an atomic position, and an orientation;
   modeling, using a processor, a plurality of reactions involving one or more of the molecular structures, wherein the plurality of reactions comprise at least one of an on-wall ineffective collision, a decomposition, an inter-molecular ineffective collision, and a synthesis, wherein selecting, using the processor, each reaction in the plurality of reactions comprises:
   determining a random number;
   determining if the random number is less than an inter-molecular reaction parameter;
   modeling an on-wall ineffective collision of a molecular structure;
   determining if a sum of the potential energy value and kinetic energy value of the molecular structure is greater than a new potential energy value of the molecular structure after the on-wall ineffective collision based upon a determination that the random number is less than the inter-molecular reaction parameter;
   allowing the on-wall ineffective collision based upon a determination that the sum is greater than the new potential energy;
   determining the molecular structure has stayed in a stable state for at least a predetermined period of time based upon the determination that the sum is less than the new potential energy value;
   decomposing the molecular structure into two or more molecular structures based upon the determination that the molecular structure has stayed in the stable state for at least the predetermined period of time; and
   modeling an inter-molecular collision based upon a determination that the random number is greater than the inter-molecular reaction parameter, wherein the inter-molecular collision is a synthesis or an inter-molecular ineffective collision;

determining, after each of the plurality of reactions, an energy value of the molecular structures based upon the potential energy values and kinetic energy values of the molecular structures;

storing the molecular structures when the energy value is less than a previously stored energy value;

determining a stopping criteria is met; and determining the solution for the objective function as the stored molecular structures that has the lowest energy value that corresponds to the global minimum.

4. The method of claim 3, wherein the objective function comprises a non-deterministic polynomial-time hard (NP-hard) problem.

5. A non-transitory computer-readable medium having instructions stored thereon, the instructions comprising:

instructions to obtain an objective function that is subject to constraints and a number of possible solutions to the objective function;

assign molecular structures and chemical reaction parameters to a plurality of reactant molecules, wherein the molecular structures comprise a kinetic energy value, a potential energy value, an atomic position, and an orientation;

instructions to model a plurality of reactions involving one or more of the molecular structures, wherein the plurality of reactions comprise at least one of an on-wall ineffective collision, a decomposition, an inter-molecular ineffective collision, and a synthesis, wherein to select each reaction in the plurality of reactions comprises:

instructions to determine a random number;

instructions to determine if the random number is less than an inter-molecular reaction parameter;

instructions to model an on-wall ineffective collision of a molecular structure;

instructions to determine if a sum of the potential energy value and kinetic energy value of the molecular structure is greater than a new potential energy value of the molecular structure after the on-wall ineffective collision based upon a determination that the random number is less than the inter-molecular reaction parameter;

instructions to allow the on-wall ineffective collision based upon a determination that the sum is greater than the new potential energy;

instructions to determine the molecular structure has stayed in a stable state for at least a predetermined period of time based upon the determination that the sum is less than the new potential energy value;

instructions to decompose the molecular structure into two or more molecular structures based upon the determination that the molecular structure has stayed in the stable state for at least the predetermined period of time; and instructions to model an inter-molecular collision based upon a determination that the random number is greater than the inter-molecular reaction parameter, wherein the inter-molecular collision is a synthesis or an inter-molecular ineffective collision;

instructions to determine, after each of the plurality of reactions, an energy value of the molecular structures based upon the potential energy values and kinetic energy values of the molecular structures;

instructions to store the molecular structures when the energy value is less than a previously stored energy value;

instructions to determine a stopping criteria is met; and instructions to determine the solution for the objective function as the stored molecular structures that has the lowest energy value that corresponds to the global minimum.

6. The non-transitory computer-readable medium of claim 5, wherein the objective function comprises a non-deterministic polynomial-time hard (NP-hard) problem.

7. The apparatus of claim 1, wherein the objective function defines a potential energy surface of a chemical system comprising the reactant molecules.

8. The apparatus of claim 7, wherein the reactions represent different parts of the potential energy surface.

9. The method of claim 3, wherein the objective function defines a potential energy surface of a chemical system comprising the reactant molecules.

10. The method of claim 9, wherein the reactions represent different parts of the potential energy surface.

11. The non-transitory computer-readable medium of claim 5, wherein the reactions represent different parts of the potential energy surface.

12. The non-transitory computer-readable medium of claim 11, wherein the reactions represent different parts of the potential energy surface.

13. The apparatus of claim 1, wherein to model the inter-molecular collision the one or more processors are configured to:

determine a sum of potential energy values and kinetic energy values of two or more molecular structures;

model a synthesis of the two or more molecular structures to form a new molecular structure;

determine the sum of potential energy values and kinetic energy values is greater than a new potential energy value of the new molecular structure; and allow the synthesis based upon the determination that the sum of potential energy values and kinetic energy values is greater than the new potential energy value of the new molecular structure.

14. The apparatus of claim 1, wherein to model the inter-molecular collision the one or more processors are configured to:

determine a sum of potential energy values and kinetic energy values of two or more molecular structures;

model an inter-molecular ineffective collision between the two or more molecular structures;

determine the sum of potential energy values and kinetic energy values is greater than a sum of the potential energy values of the two or more molecular structures after the inter-molecular ineffective collision; and allow the inter-molecular ineffective collision based upon the determination that the sum of potential energy values and kinetic energy values is greater than a sum of the potential energy values of the two or more molecular structures after the inter-molecular ineffective collision.

15. The method of claim 3, wherein the modeling the inter-molecular comprises:

determining a sum of potential energy values and kinetic energy values of two or more molecular structures;

modeling a synthesis of the two or more molecular structures to form a new molecular structure;

determining the sum of potential energy values and kinetic energy values is greater than a new potential energy value of the new molecular structure; and allowing the synthesis based upon the determination that the sum of potential energy values and kinetic energy values is greater than the new potential energy value of the new molecular structure.

16. The method of claim 3, wherein the modeling the inter-molecular collision comprises:
- determining a sum of potential energy values and kinetic energy values of two or more molecular structures;
- modeling an inter-molecular ineffective collision between the two or more molecular structures;
- determining the sum of potential energy values and kinetic energy values is greater than a sum of the potential energy values of the two or more molecular structures after the inter-molecular ineffective collision; and
- allowing the inter-molecular ineffective collision based upon the determination that the sum of potential energy values and kinetic energy values is greater than a sum of the potential energy values of the two or more molecular structures after the inter-molecular ineffective collision.

17. The non-transitory computer-readable medium of claim 5, wherein the instructions to model the inter-molecular collision comprise:
- instructions to determine a sum of potential energy values and kinetic energy values of two or more molecular structures;
- instructions to model a synthesis of the two or more molecular structures to form a new molecular structure;
- instructions to determine the sum of potential energy values and kinetic energy values is greater than a new potential energy value of the new molecular structure; and
- instructions to allow the synthesis based upon the determination that the sum of potential energy values and kinetic energy values is greater than the new potential energy value of the new molecular structure.

18. The non-transitory computer-readable medium of claim 5, wherein the instructions to model the inter-molecular collision comprise:
- instructions to determine a sum of potential energy values and kinetic energy values of two or more molecular structures;
- instructions to model an inter-molecular ineffective collision between the two or more molecular structures;
- instructions to determine the sum of potential energy values and kinetic energy values is greater than a sum of the potential energy values of the two or more molecular structures after the inter-molecular ineffective collision; and
- instructions to allow the inter-molecular ineffective collision based upon the determination that the sum of potential energy values and kinetic energy values is greater than a sum of the potential energy values of the two or more molecular structures after the inter-molecular ineffective collision.

* * * * *

UNITED STATES PATENT AND TRADEMARK OFFICE
CERTIFICATE OF CORRECTION

| | |
|---|---|
| PATENT NO. | : 8,706,423 B2 |
| APPLICATION NO. | : 12/498085 |
| DATED | : April 22, 2014 |
| INVENTOR(S) | : Li et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 989 days.

Signed and Sealed this
Eleventh Day of August, 2015

Michelle K. Lee
*Director of the United States Patent and Trademark Office*